(12) United States Patent
Pratt

(10) Patent No.: US 6,846,028 B2
(45) Date of Patent: Jan. 25, 2005

(54) DUAL FUNCTION BAILER

(76) Inventor: David W. Pratt, 13512 Feather Sound Cir. West, Apt. 1401, Clearwater, FL (US) 33760

( * ) Notice: Subject to any disclaimer, the term of this patent is extended or adjusted under 35 U.S.C. 154(b) by 0 days.

(21) Appl. No.: 09/681,814

(22) Filed: Jun. 11, 2001

(65) Prior Publication Data

US 2002/0185878 A1 Dec. 12, 2002

(51) Int. Cl.[7] .............................................. G01N 1/10
(52) U.S. Cl. ................................ 294/68.25; 73/864.63; 73/864.91
(58) Field of Search ................... 294/68.25; 73/864.31, 73/864.51, 864.63, 864.86, 864.91; 166/162

(56) References Cited

U.S. PATENT DOCUMENTS

| | | | |
|---|---|---|---|
| 4,590,810 A | * 5/1986 | Hunkin et al. ........... 73/864.63 |
| 4,625,574 A | 12/1986 | Robbins | |
| 5,431,884 A | * 7/1995 | McDonough et al. ....... 422/101 |
| 5,597,966 A | * 1/1997 | Timmons .................. 73/864.63 |
| 5,878,813 A | * 3/1999 | Ridgeway, Jr. .............. 166/162 |

* cited by examiner

Primary Examiner—Dean J. Kramer
(74) Attorney, Agent, or Firm—Ronald E. Smith; Smith & Hopen, P.A.

(57) ABSTRACT

An upper imperforate cap closes the uppermost end of a bailer and a lower imperforate cap closes the lowermost end of the bailer. In a preferred embodiment, screwthreads are formed in the uppermost and lowermost ends of the bailer and complemental screwthreads are formed in the upper and lower caps. In another embodiment, screwthreads are formed in a downspout and complemental screwthreads are formed in an imperforate downspout cap. By capping the opposite ends of a bailer, the bailer serves as its own container when the sample contained within it is shipped to a laboratory. This eliminates VOC devices, nozzles, and the concomitant contamination that may result from emptying a bailer in the field.

1 Claim, 2 Drawing Sheets

DUAL FUNCTION BAILER

BACKGROUND OF INVENTION

1. Field of the Invention

This invention relates, generally, to bailers. More particularly, it relates to a bailer that performs the function of a bailer and of a sample container.

2. Description of the Prior Art

All conventional bailers require emptying into a sample container shortly after a sample has been taken from a body of water or other liquid fluid. The sample container is then placed in a cooler and transported to a lab so that the sample can be analyzed.

Most workers in the field simply invert the bailer to empty it. This emptying procedure is unacceptable, however, because it allows oxygen to enter the liquid fluid, thereby resulting in false data. Moreover, the pouring action agitates the liquid fluid.

To encourage workers in the field to empty bailers without inverting them, numerous emptying devices have been developed that lift the valve at the lowermost end of the bailer from its valve seat. The most common emptying device is a nozzle; another well-known device is known in the industry as a VOC emptying device.

VOC devices, nozzles, and other emptying devices also add expense to the bailer manufacturing process.

Inventors in the bailer field have developed numerous emptying devices, but the problems associated therewith persist. What is needed is an innovation that provides an answer to the bailer emptying problem.

However, in view of the prior art considered as a whole at the time the present invention was made, it was not obvious to those of ordinary skill in the pertinent art how the answer could be provided.

SUMMARY OF INVENTION

The longstanding but heretofore unfulfilled need for an improved bailer that eliminates the contamination that may arise from in-the-field bailer emptying is now met by a new, useful, and nonobvious bailer construction. The novel construction includes a bailer having an elongate tubular body that has a first or upper end and a second or lower end. The second end has a one-way valved opening so that liquid fluid may flow into the elongate tubular body when the bailer is immersed in a body of liquid fluid and so that liquid fluid is substantially prevented from flowing out of the elongate tubular body when the bailer is lifted from the body of liquid fluid.

In a first embodiment, an imperforate cap is adapted to fit onto the second, lower end of the elongate tubular body. The imperforate cap prevents liquid fluid from flowing out of the second end of the elongate tubular body independently of the position of the bailer.

Screwthreads are formed in the second end and complemental screwthreads are formed in the imperforate cap so that the imperforate cap is selectively screwthreadedly engageable and disengageable to the second end. NPT threads are preferred.

An imperforate cap is also adapted to fit onto the first, uppermost end of the elongate tubular body. The imperforate cap prevents liquid fluid from flowing out of the first end of the elongate tubular body independently of the position of the bailer. A smaller in diameter cap is used at the uppermost end of the bailer in those bailer designs where the top end is tapered downwardly to have a smaller diameter than the diameter of the elongate tubular body.

Screwthreads are formed in the first end of the elongate tubular member and complemental screwthreads are formed in the imperforate cap so that the imperforate cap is selectively screwthreadedly engageable and disengageable to the first end.

Where the bailer is of the type having a downspout that depends from the second end of the elongate tubular member, an alternative embodiment of the invention provides an imperforate cap adapted to fit onto the downspout. The imperforate cap prevents liquid fluid from flowing out of the downspout independently of the position of the bailer.

Screwthreads are formed in the downspout and complemental screwthreads are formed in the imperforate cap so that the imperforate cap is selectively screwthreadedly engageable and disengageable to the downspout.

In all embodiments, a press fit, snap fit, or any other suitable alternative to screwthreads may be used to releasably engage the imperforate cap to the tubular main body or downspout.

Accordingly, when a sample has been taken, the user need not employ a VOC device, nozzle, or other bailer-emptying device to transfer the contents of the bailer into a sample container. No device of any kind is used to empty the bailer in the field. Instead, the appropriate caps are secured to the bailer, and the bailer itself is shipped to a laboratory. Thus, the bailer serves the dual function of a bailer and as a sample container. In this way, the bailer may be emptied in a sterile laboratory free of contamination possibilities.

A primary object of the invention is to provide a highly innovative, revolutionary answer to the longstanding bailer-emptying problem.

A closely related object is to attain the foregoing object with a bailer construction that provides a bailer that is not emptied in the field.

Another closely related object is to provide a bailer that is emptied only after it has reached a laboratory.

Yet another object is to provide a bailer that reduces contamination of a sample by eliminating any added oxygen of the type caused by pouring collected liquid fluid from the uppermost end of the bailer or by using an emptying device that empties the bailer from its lowermost end, such contamination causing incorrect sample data, i.e., producing false readings.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
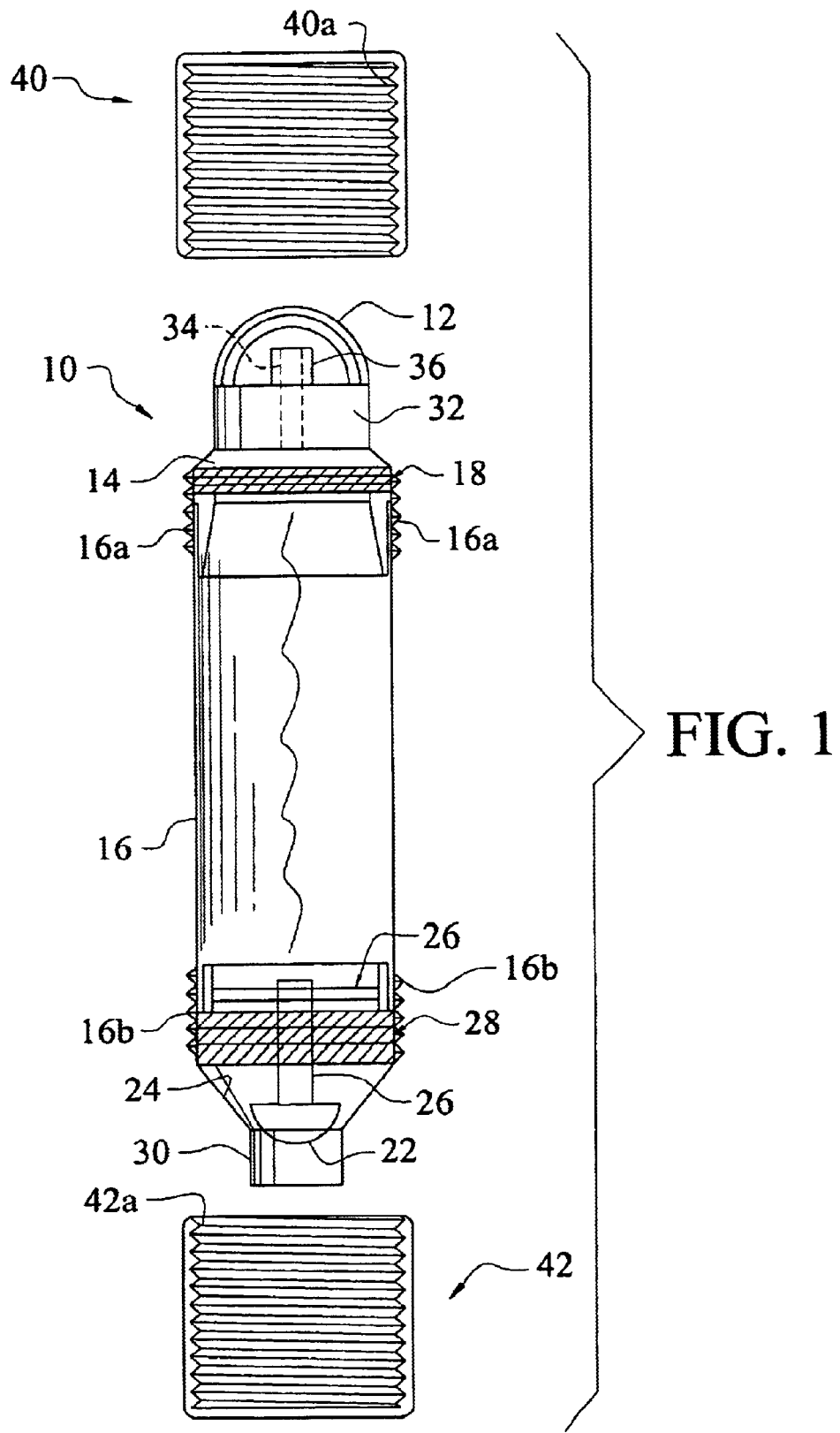
FIG. 1 is an exploded side elevational view of an illustrative embodiment of the invention.

Referring to FIG. 1, it will there be seen that the reference numeral 10 denotes an illustrative embodiment of the present invention.

The invention has utility with bailers of all types. It will be described first in connection with a bailer having more features than a conventional bailer, just to make it clear that the novel structure will work with sophisticated bailers as well as common bailers having no extra features.

Bailer 10 includes handle 12 at its uppermost end to which is secured a rope, not shown, to enable the lowering and lifting of the bailer into and from a body of liquid fluid. In this sophisticated bailer embodiment, a weight housing 14 is slidingly received within tubular main body 16 of the bailer and provides a means for holding top weight members, collectively denoted 18.

A spider assembly 20 is positioned near the lower end of tubular main body 16 and serves to guide hemispherical valve body or check ball 22 as it rises and falls with respect to valve seat 24. Valve stem 26 is slidingly received within an aperture formed in the center of spider assembly 20 so that check ball 22 rises and separates from valve seat 24 when liquid fluid flows into the interior of tubular main body 16 and so that said check ball returns to its seated position against valve seat 24 when said liquid fluid stops flowing into said tubular main body.

A lower set of weights, collectively denoted 28, is provided near the lowermost end of bailer 10, and a tubular fluid entry/discharge spout or downspout 30 depends from valve seat 24.

In this particular embodiment, plug 32 having a vent opening 34 formed therethrough closes the uppermost end of weight housing 14 (or the uppermost end of tubular main body 16 in less advanced bailers lacking such weight housing). In this embodiment, vent opening 34 is formed in boss 36 that is formed integrally with plug 32. For a more detailed description of the operation of this advanced design bailer, see a co-pending disclosure filed by the present inventor on Feb. 2, 2001, bearing Ser. No. 09/776,468, entitled "Controlled Slow Descent Bailer," now U.S. Pat. No. 6,431,272 which disclosure is hereby incorporated by reference into this disclosure.

Screwthreads 16a are formed in the uppermost end of tubular main body 16 and screwthreads 16b are formed in the lowermost end of said tubular main body. Imperforate upper cap 40 has complementally formed screwthreads 40a formed in its inner cylindrical sidewalls that screwthreadedly engage screwthreads 16a. Similarly, imperforate lower cap 42 has complementally formed screwthreads 42a formed in its inner cylindrical sidewalls that screwthreadedly engage screwthreads 16b. Instead of inverting the bailer to empty it from its uppermost end, which is the most common practice in the field, and instead of using a VOC device or nozzle to lift check ball 22 from valve seat 24 as required when emptying a prior art bailer without inverting it, upper cap 40 is screwthreadedly engaged to threads 16a and lower cap 42 is screwthreadedly engaged to threads 16b as soon as bailer 10 is retrieved from the sampled body of liquid fluid. Bailer 10 is then transported to a lab. No contamination of its contents can arise in the process of emptying the bailer in the field into a container because no such emptying takes place. Instead, the bailer is emptied by laboratory personnel in sterile laboratory conditions.

Figure 2:
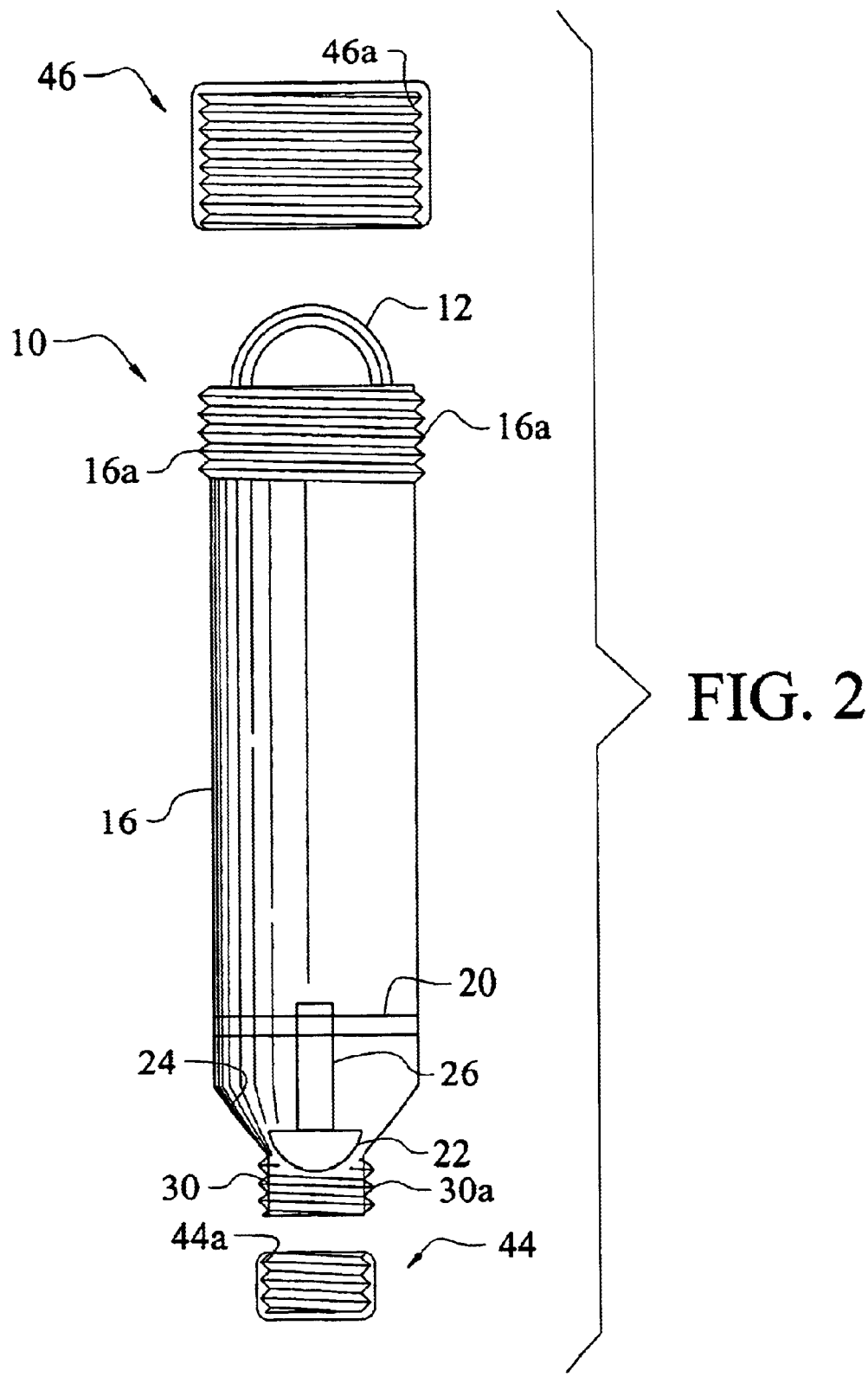
FIG. 2 is an exploded side elevational view of a second embodiment.

FIG. 2 depicts an unweighted bailer. In this embodiment, screwthreads 30a are formed in downspout 30. A smaller-in-diameter cap 44 having complementally formed screwthreads 44a is used as an alternative to lower cap 42. Cap 44 also has less depth than lower cap 42 since it need not accommodate valve seat 24 and downspout 30.

Similarly, since the bailer of FIG. 2 lacks weight housing 14 and boss 36, upper cap 46 is also of less depth than upper cap 40 because it need not accommodate such parts.

It should be understood that smaller cap 44 could also be used in the FIG. 1 embodiment in lieu of cap 42. Moreover, the caps may be press fit, snapped onto, or otherwise releasably engaged to their respective parts of the bailer, it being understood that this invention is not limited to the use of screwthreaded engagement means.

A smaller cap such as cap 44 would also be used at the uppermost end of the bailer in those bailer designs where the top end is tapered downwardly to have a smaller diameter than the diameter of the elongate tubular body.

This improvement is a revolutionary improvement in the art of bailers. No ground water sampling bailer has heretofore served as its own container, i.e., no such bailer has heretofore been shipped to a laboratory while filled with a sample of liquid fluid to be analyzed. The invention thus renders superfluous both VOC devices, nozzles and the containers that receive the contents of a bailer. It further eliminates the possibility of contamination during the bailer emptying procedure that heretofore always took place in the field. Moreover, the caps of this invention are less expensive to manufacture than VOC devices or nozzles, thereby making this greatly improved bailer even less expensive than its less desirable predecessors.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,
What is claimed is:

1. A bailer, comprising:
an elongate tubular body having an externally threaded uppermost end and an externally threaded downspout;
a handle mounted to said externally threaded uppermost end, said handle protruding upwardly from said uppermost end of said elongate tubular body;
a first internally threaded imperforate cap adapted to fit onto said externally threaded uppermost end of said elongate tubular body, said first imperforate cap preventing liquid fluid from flowing out of said uppermost end independently of the position of the bailer;
said first internally threaded imperforate cap having a depth sufficient to accommodate said handle;
said second end having a one-way valved opening so that liquid fluid may flow into said elongate tubular body when said bailer is immersed in a body of liquid fluid and so that said liquid fluid is substantially prevented from flowing out of said elongate tubular body when said bailer is lifted from said body of liquid fluid;
a second internally threaded imperforate cap adapted to fit onto said externally threaded downspout, said second internally threaded imperforate cap preventing liquid fluid from flowing out of said externally threaded downspout independently of the position of the bailer.

* * * * *